United States Patent [19]

Stefancin, Jr.

[11] Patent Number: 5,562,625

[45] Date of Patent: Oct. 8, 1996

[54] REUSASBLE SYRINGE WITH A DISPOSABLE NEEDLE SHEATH

[76] Inventor: Ronald J. Stefancin, Jr., 30412 Center Ridge Rd., Westlake, Ohio 44145

[21] Appl. No.: 431,681

[22] Filed: May 2, 1995

[51] Int. Cl.$^6$ ........................................ A61M 5/00
[52] U.S. Cl. ........................ 604/110; 604/198; 604/263
[58] Field of Search .................................. 604/110, 187, 604/192, 198, 263

[56] References Cited

U.S. PATENT DOCUMENTS

| | | | |
|---|---|---|---|
| 4,842,587 | 6/1989 | Poncy | 604/198 |
| 5,181,524 | 1/1993 | Wanderer et al. | 604/198 X |
| 5,222,947 | 6/1993 | D'Amico | 604/263 X |

*Primary Examiner*—John D. Yasko
*Attorney, Agent, or Firm*—Joseph H. Taddeo

[57] ABSTRACT

A one-piece safety sheath for sliding over a standard syringe body having an ampule for liquids and a plunger for forcing liquids out of the ampule and drawing them in. The sheath is capped to store a needle and needle assembly within in sterile condition, to stabilize the needle during use, and to store the spent needle in locked position within the sheath following use.

12 Claims, 7 Drawing Sheets

REUSASBLE SYRINGE WITH A DISPOSABLE NEEDLE SHEATH

The inventor herein has heretofore a first Disclosure Document for the first embodiment of his invention on Apr. 28, 1993, identified by number 333275, and a copy of same is enclosed for inclusion in this utility patent application file.

Meanwhile, your applicant also filed a second Disclosure Document for the preferred embodiment of his invention on May 28, 1993, identified by Disclosure Document number 331793, and a copy of same is also enclosed for inclusion in this patent application file.

FIELD OF INVENTION

The present invention relates to a syringe that is reusable and more particularly to one that uses a disposable sheathed metallic conduit which is housed in a safety tube after use, thereby reducing the possibility of accidental infection by used needles.

BACKGROUND OF THE INVENTION

Hypodermic syringes, complete with a hollow needle have been used for the injection and administration of medicaments as well as to draw blood. The size of the needle and its associated syringe may vary depending upon the intended use.

The needle itself is a sharp hollow metallic tube that is designed to penetrate the skin of the patient while providing the east amount of discomfort. The needle, if not properly stored can become a potentially dangerous instrument. Once a needle is used, it must be sterilized before reuse, otherwise it must be safely disposed of.

One of the potential dangers after use is the possibility of infection for medical personnel by accidental needle sticks. If the needle is not properly stored or disposed of, one can become seriously infected by viruses or other bacterial agents. Even a trained medical technician is at risk when the necessary safety procedures are not followed.

Still another danger is one where the patient can be reinfected through the inadvertent reuse of a needle that has not been sterilized. These are especially important considerations today to prevent the spread of contagious diseases such as Aids.

SUMMARY OF THE INVENTION

The present invention in its preferred embodiment consists of a plunger-type syringe to which is coupled a needle assembly that is easily disconnected after use. The needle assembly is housed in a clear transparent plastic cylindrical safety tube or safety sheath equipped with protective removable end caps. The safety tube is an inexpensive and efficient means of (1) preventing reuse of a spent needle and of (2) reducing the possibility of accidental infection to medical attendants by used needles.

The needle is captivated into a hollow nylon piece that provides two male threads that are oppositely disposed that engage into the syringe's female double-threaded bushing. This needle assembly is capable of moving longitudinally and is guided by two slots formed on the inside of the safety tube.

There are three unique positions of the needle assembly within the safety sheath: the first position is its initial position, indicating the needle is in sterile condition; the second position is its in-use position at its extreme opposite end; the third position being a locked and spent position, indicating that it is no longer sterile and must not be reused.

In its typical use the medical attendant first removes the end cap located near the threaded end of the needle assembly. He then screws the needle on the end of the syringe while the needle assembly is in its initial position within the safety tube. The second safety cap at the opposite end is removed and the safety tube is slid back over the syringe's body into the stops, readying the needle for use.

After use, the safety tube or sheath is carefully slid longitudinally over the extended needle until it snaps in place. The end cap is placed on the needle end of the safety tube. The attendant unscrews the safety sheath from the body of the syringe and replaces the second end cap.

With the needle locked into its spent position, one can readily observe that the needle has been used. The locked position prevents its reuse. However, if required by medical administrators, trained medical personnel can remove the spent needle from the safety sheath and sterilize it, readying it for subsequent reuse.

It is therefore an object of this invention to provide a hypodermic needle assembly that consists of two subassemblies; a reusable syringe and a disposable hollow needle that is stored in a safety sheath.

It is another object of this invention to provide for a hypodermic needle assembly, where the needle in its safety sheath can be easily disconnected from the body of the syringe.

It is still another object of this invention to provide needle stop and storage positions for the needle within the safety tube. The first position being for the initial use of the sterile needle; the second position being a position stabilizing the needle while in use; and the third position being a locked, spent position indicating that the needle has been used and is no longer sterile.

Yet another object of this invention is to provide for a safety sheath that allows needle removal from the safety sheath. By snapping the needle out of its safety tube, it now can be reused by sterilizing the needle.

A further object is to provide a transparent sheath, whereby medical attendants can see the needle position within the sheath to know whether that particular needle remains sterile.

Lastly, it is another object of this invention to provide a means of preventing accidental infection which is inexpensive, reliable and safe in its use.

These and other objects of the invention which are achieved by the present invention, will become apparent from the detailed description to follow, taken in conjunction with the accompanying drawings.

BRIEF DESCRIPTION OF THE DRAWINGS

FIG. 11 A is a cutaway side view of the sheath.

FIG. 11 B is section view of the sheath taken along line 11—11 of FIG. 11 A

DETAILED DESCRIPTION OF THE PREFERRED EMBODIMENT

Figure 1A:
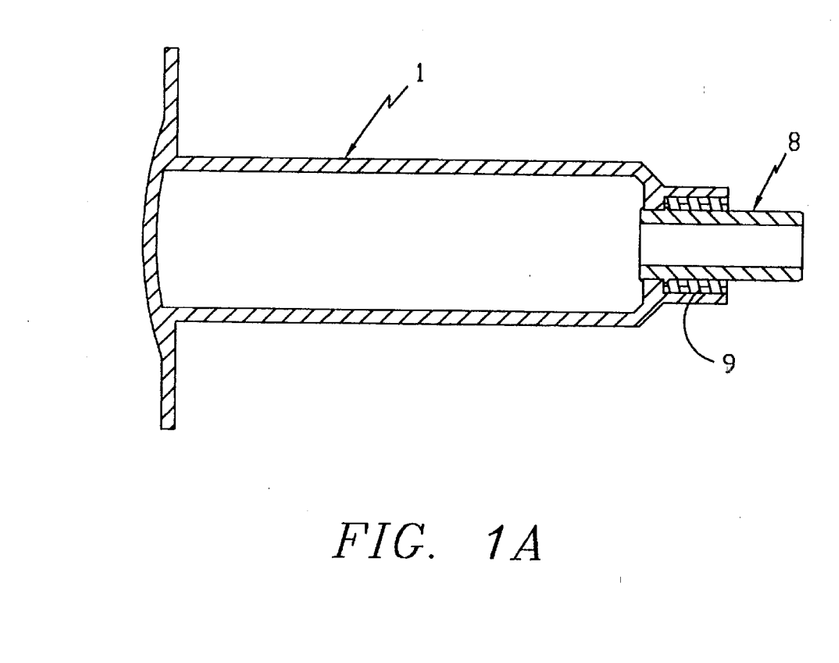
FIG. 1 is a longitudinal sectional view of the syringe subassembly that is shown near the safety tube which houses the disposable needle. The safety tube is shown with protective end caps. The needle is illustrated in the temporary storage position before use.
Figure 1B:
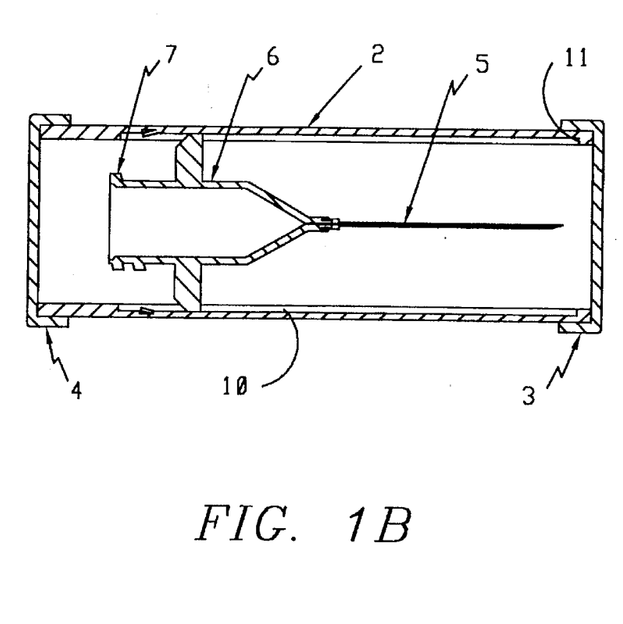

As is shown in FIG. 1, the implementation of a first embodiment of the present invention, uses a standard off-the-shelf plunger type syringe 1 formed as an ampule with a chamber for connection with a sterilized needle 5 fixed in a needle transport assembly 6.

Also shown in FIG. 1, in proximity to syringe 1 is the safety sheath or tube 2. End caps 3 and 4 close off each end of safety sheath 2, thereby maintaining the integrity of the contents of the safety sheath. By closing each end of the safety sheath with the end caps, the sterilized needle 5 and needle transport assembly 6 remain free from contaminants for maintenance of a sterile condition.

Figure 3:
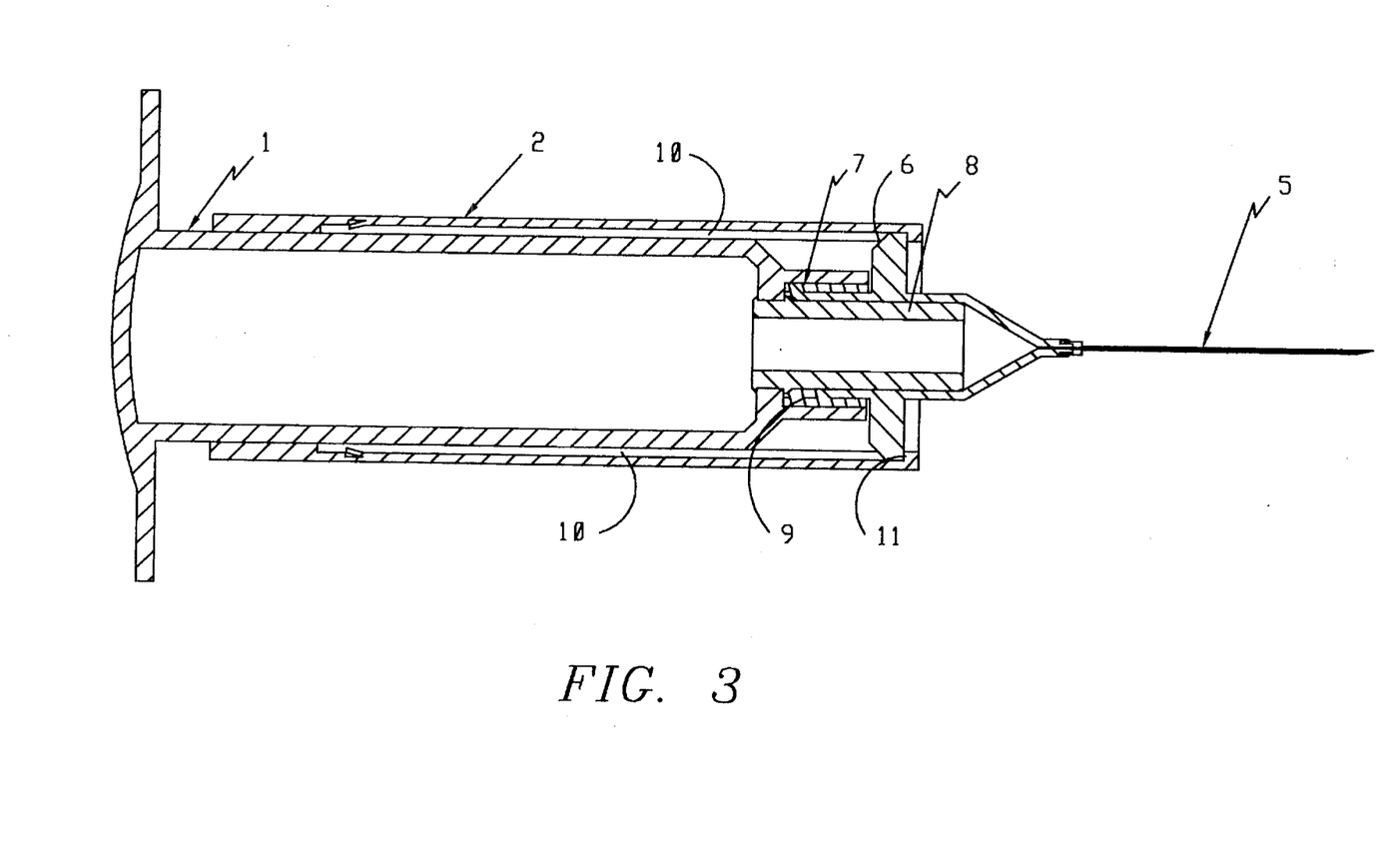
FIG. 3 is a cutaway view of the syringe subassembly with the hypodermic needle fully engaged with the syringe. The safety tube is shown fully retracted over the body of the syringe. The needle is shown in the stopped position.
Figure 7:
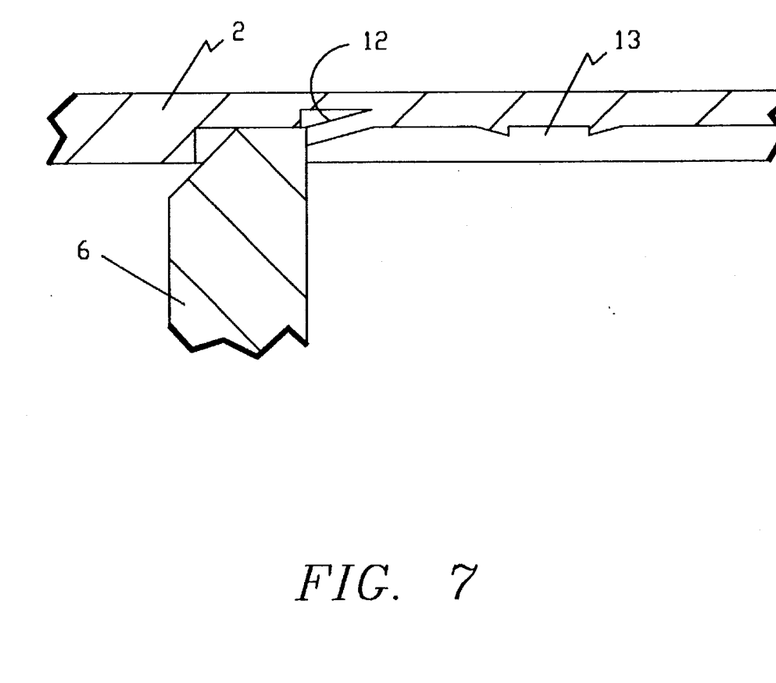
FIG. 7 is a detailed exploded view of the locking mechanism showing the needle transport assembly in the locked position.

The safety sheath 2 is adapted for temporarily anchoring the needle transport assembly 6 at one of three stop positions, a first, sterilized needle position, FIG. 1; a second, needle in-use position, FIG. 3; and a third, locked and spent needle position, FIG. 7.

The sheath 2, which is preferably constructed of a transparent polymer material, allows for visual checking and confirmation by medical personnel as to whether the needle is sterile, (first position), or whether the needle has already been used, (third position).

Figure 11A:
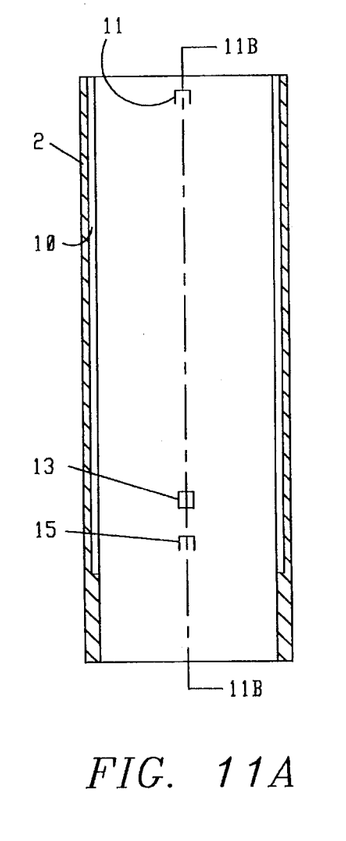
Figure 11B:
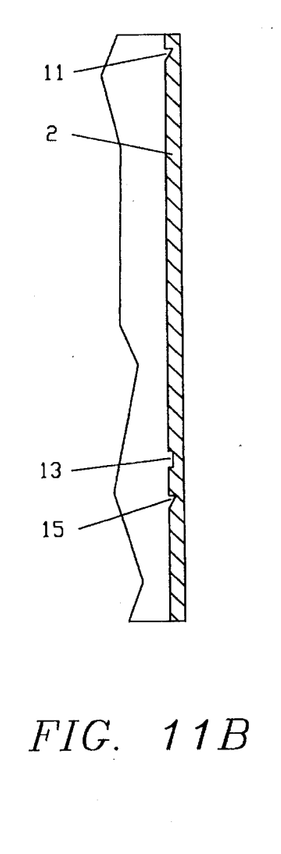

The positioning stop tabs 13 which hold the needle transport assembly in its initial position is best observed in FIG. 7 and FIGS. 11–11A.

Figure 2:
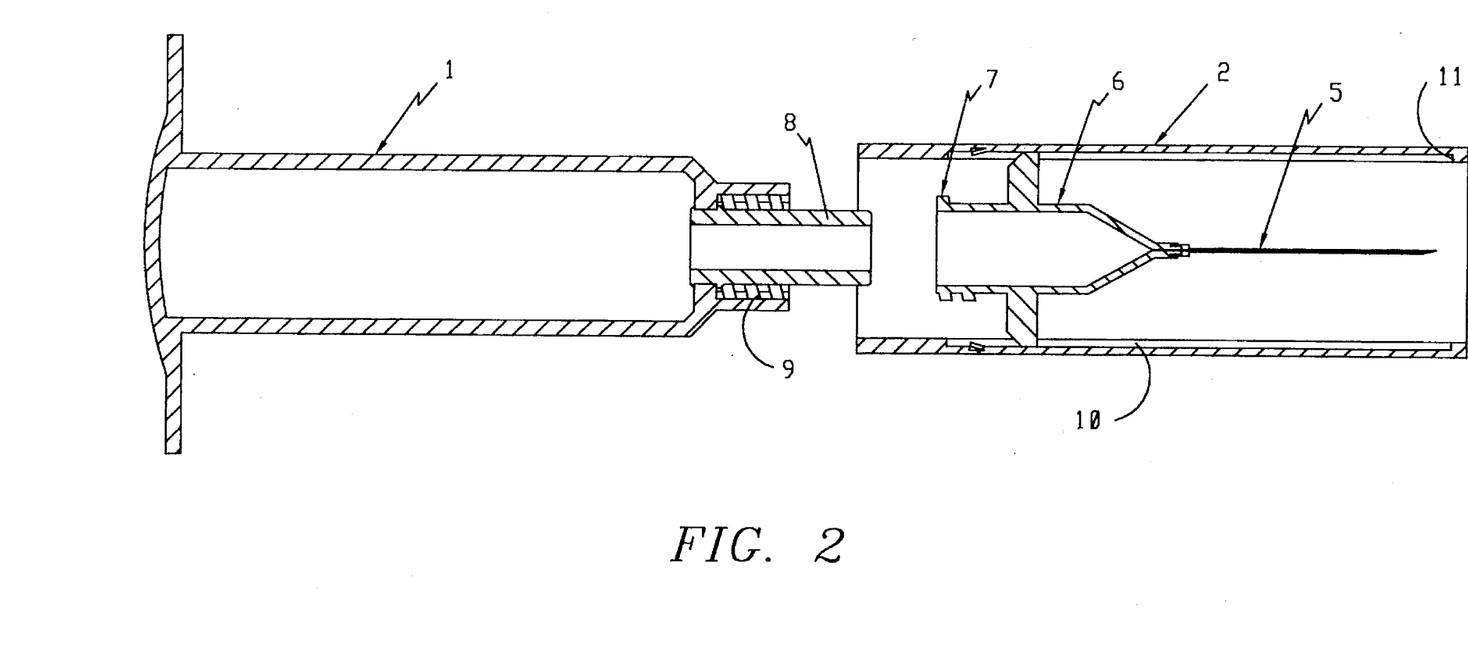
FIG. 2 is a longitudinal section of the syringe subassembly that is shown in proximity of the safety tube, protective end caps removed, which tube houses the disposable needle. The safety tube is shown with the protective end caps removed.

FIG. 2 shows the safety sheath 2 ready to be engaged to the body of the syringe 1. The protective end caps 3 and 4 have been removed and set aside for use after the injection has been made. The needle assembly 6 remains in its initial storage position 13 within the safety tube 2.

Proceeding to FIG. 3, the hypodermic needle assembly is shown fully prepared, ready for use.

To prepare it for use, the threaded end of the needle transport assembly, which bears luer 17, and struts or male threads 7 are guided over the protruding column 8 of the syringe, then threaded into the female threaded bushing of the syringe body 9 by rotating the safety sheath in a clockwise direction (right-handed thread). Rotating the syringe body 1 also rotates the needle assembly 6, because the needle transport assembly guides 6 are held within the longitudinal rectangularly shaped slots 10. These slots are best illustrated in an exploded view, as shown in FIG. 7. Once the threads are fully engaged by bottoming out, the safety sheath 2 is slid back over the body of the syringe 1 until it comes to rest against stops 11. The needle 5 is now fully exposed and the hypodermic syringe with needle is now ready for use.

Figure 4A:
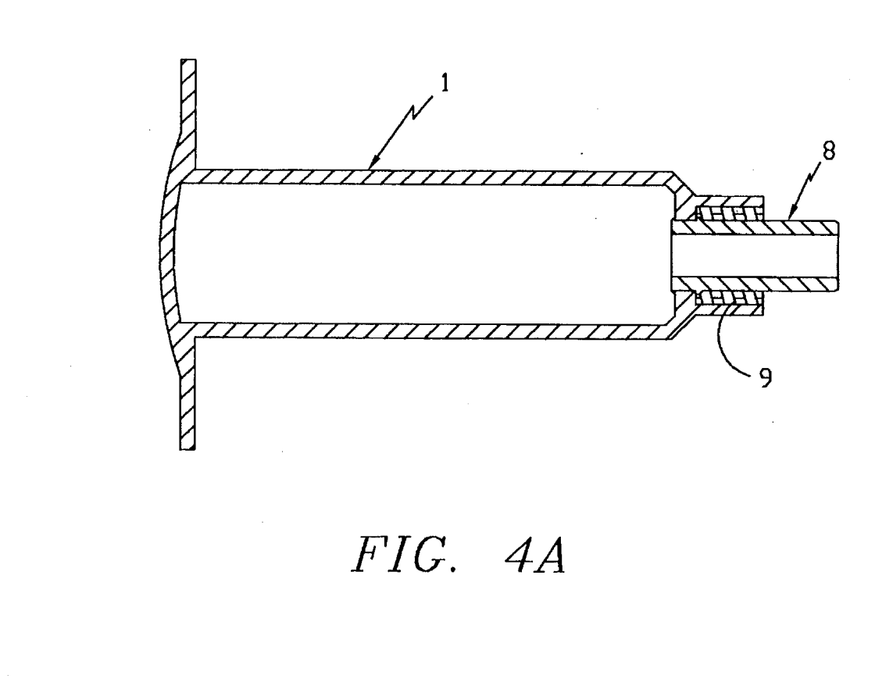
FIG. 4 is a sectional view of the syringe subassembly after use. The safety tube is shown near the syringe with the needle locked in the used position and disengaged from the syringe; the protective end caps not yet placed on the safety tube.
Figure 4B:
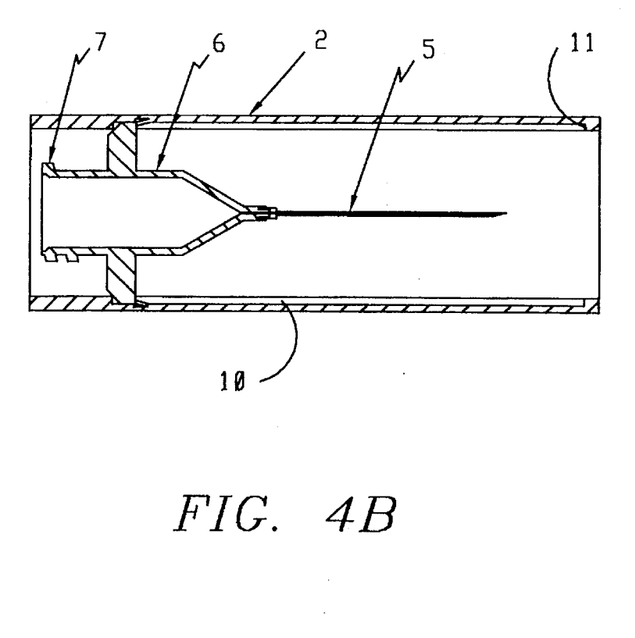

Once the needle injection has been made, the safety sheath 2 is slid forward, away from the syringe body 1, until the needle transport assembly 6 is locked into place. The locked position is shown in FIG. 7, where the locking cusps 12 prevent the needle transport assembly 6 from moving. The entire safety tube assembly 2 is then unthreaded from the syringe body 1. FIG. 4 shows the safety tube assembly 2 unscrewed from the syringe body 1. The needle assembly 6 is locked in the spent position by locking cusps 12.

Figures 8, 9, 10:
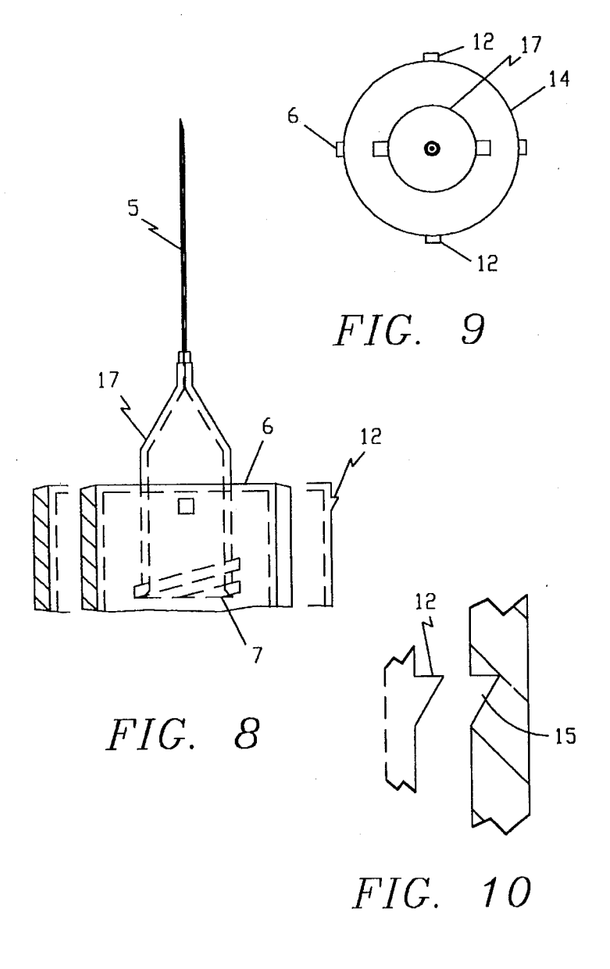
FIG. 8 is a side plan of the needle transport assembly indicating the luer and cusps protruding outward from the peripheral edge.
FIG. 9 is a top plan of the needle transport assembly with peripheral edge tabs and cusps.
FIG. 10 is an exploded view of the cusp and locking stop formed in the sheath.

A pair of locking cusps 12 may be formed from the inner sheath wall, arising from that wall to project toward the sheath body end, as seen in FIG. 7, whereby the cusps are adapted to lock the needle and needle assembly 6 firmly in the spent position following use of the needle 5. However, in the preferred embodiment shown in FIGS. 8–10, locking cusps 12 protrude from the peripheral edge 14 of the needle transport assembly 6.

Reference to FIG. 11 and FIG. 11A, indicates that in the preferred embodiment, protruding cusp 12 would coincide with stop tab 13 and provide a means for anchoring the needle in a first, sterilized needle position. Protruding cusp 12 would then coincide with stop tab 11 as a means for anchoring the needle and needle transport assembly in said second, needle in-use position. And further, protruding cusp 12 would coincide with locking tab 15 for a means for anchoring the needle and needle transport assembly in said third, locked and spent needle position within the sheath.

It will be understood that the one-piece safety sheath or tube 2 disclosed here is a relatively cost efficient means for storage and preservation of needles in sterile condition and for disposition of used needles, since the sheath requires only one mold for manufacture. The sheath ends may be factory sealed with plastic or paper caps or closure of the open ends of the sheath can be achieved by shrink-wrapping.

Figure 5A:
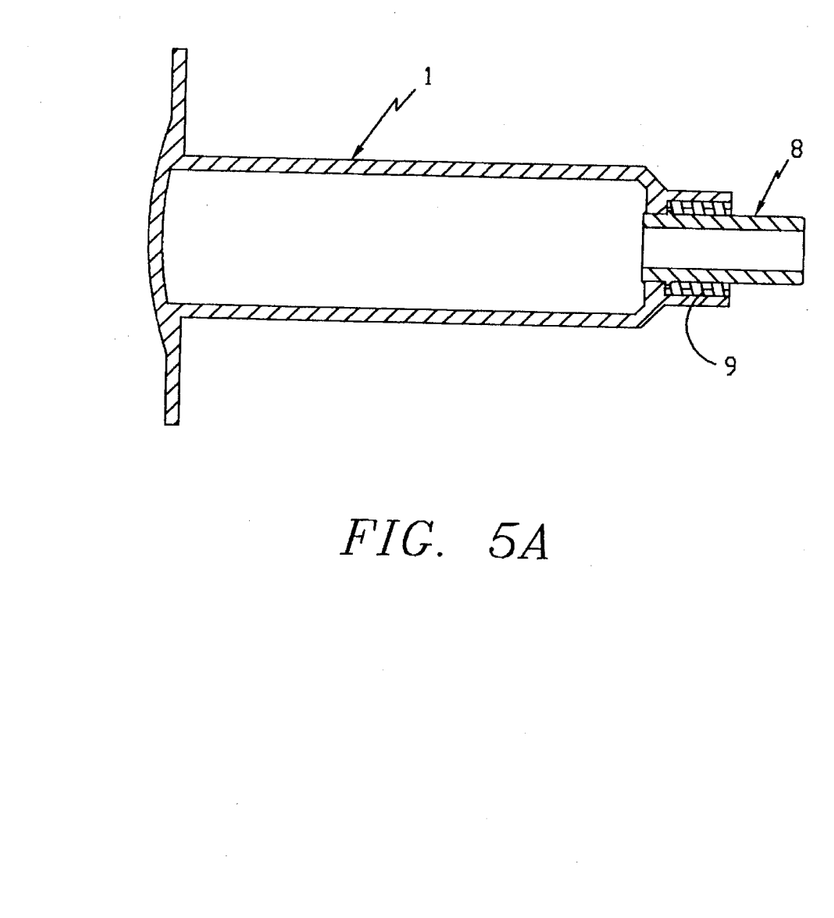
FIG. 5 shows a cutaway view of the syringe subassembly after use. Also shown near the syringe is the capped safety tube containing the needle which is locked in the spent position.
Figure 5B:
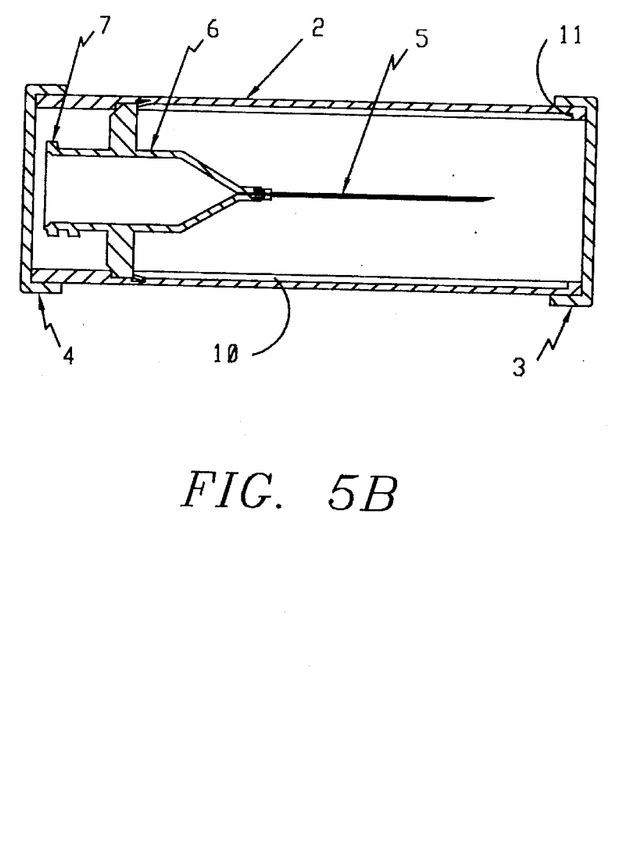
Figure 6:
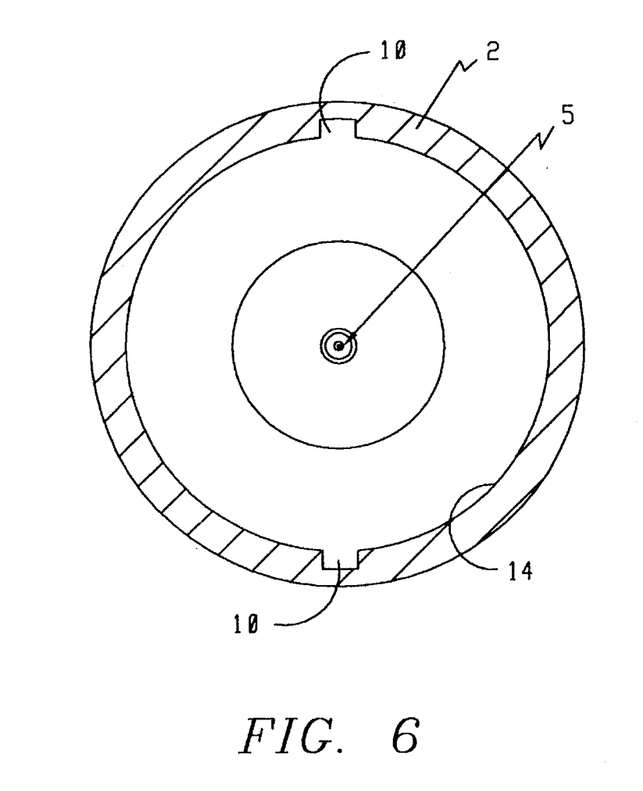
FIG. 6 is a cross-sectional view of the safety tube, showing the longitudinal, rectangular shaped slots which guide the needle transport assembly.

If constructed of paper or plastic, protective end caps 3 and 4 can be reinserted over each open end of the safety tube 2, as shown in FIG. 5. However, this is not an imperative step, for even without the end caps in place, the safety tube protects the medical attendants from coming in contact with the used needle.

The sheath is preferably constructed of a clear plastic material having translucent or, more preferably, a transparent quality. The medical attendant, by observing the locked position of the needle assembly, can readily determine that the needle has been used. If it has been used, it is readily apparent, thereby saving the patients or other potential users from infection through reuse of unsterilized needles. Trained medical attendants can then have the needle sterilized again or can dispose of it, as determined by the medical administrators.

While there have been illustrated and described what are at present considered to be preferred embodiments of the present invention, it will be understood by those skilled in the art that various changes and modifications may be made, and equivalents may be substituted for elements thereof without departing from the true scope of the present invention. In addition, many modifications may be made to adapt a particular suggestion or material to the teaching of the present invention without departing from the central scope thereof. Therefore, it is intended that the present invention not be limited to the particular embodiment disclosed as the best mode contemplated for carrying out the present invention, but that the present invention include all embodiments falling within the scope of the appended claims.

What is claimed is:

1. A hypodermic needle assembly for a sharp, tubular needle which, in a sterile condition, is designed to penetrate the skin, the assembly comprising:

a syringe assembly comprising a cylindrical ampule having a chamber, a longitudinal axis, and an open end for receiving a plunger, the plunger adapted for sliding longitudinal movement within the chamber from the open end toward a converse end of the ampule having a small orifice for fluid communication with the tubular needle for entry and exit of fluids pulled into or forced from the ampule by movement of the plunger;

a one-piece safety sheath comprising a cylindrical tube with a longitudinal axis and an inner sheath wall, the sheath having an open needle end and an open sheath body end; the ampule and said sheath each having a diameter, and the diameter of the sheath slightly greater than diameter of the ampule, whereby the sheath is adapted to fit over and slide upon the syringe body;

a needle transport assembly comprising a luer having a front portion with an elongate channel to receive and fix the needle therein; and a back portion of the luer having a means for removably connecting the needle transport assembly to the syringe; a peripheral edge of transport assembly engaging the sheath inner wall; and, the needle and needle transport assembly adapted for movement within the sheath to a stop position, and the transport assembly having three temporarily fixed stop positions, a first, sterilized needle position; a second, needle in-use position; and a third, locked and spent needle position;

a means for anchoring the needle and needle transport assembly in a stop position, said means associated with the sheath and with the needle transport assembly;

wherein the safety sheath further comprises a needle end cap and a sheath body end cap, each of the caps adapted to alternately fit on and close an open end of the sheath to maintain the sterile condition of the needle within the sheath prior to use; for removal of the caps for opening the needle end of the sheath and sheath body end of the sheath at the time for use of the needle; and, for reclosing the sheath body for needle storage within the sheath following use;

further comprising a means for maintaining the needle and needle transport coaxial with the longitudinal axis of the sheath during in the course of the needle transport assembly movement;

wherein the means for maintaining comprises a pair of opposed elongated guide slots grooved on said inner wall of the sheath body and a pair of oppositely disposed guides, each guide projecting radially from on the transport assembly peripheral edge, and each of the slots adapted to receive a guide;

wherein the guide slots are grooved as longitudinal rectangularly shaped slots;

wherein the guides have a rectangular shape complimentary to shape of the slots;

wherein the means for anchoring the needle and needle transport assembly in the first, sterilized needle position comprises a pair of opposed positioning tabs, one of said tabs grooved in each of said pair of slots, each of the tabs adapted to receive a guide and to temporarily fix the needle transport assembly in the first stop position within the sheath.

2. The assembly of claim 1, further comprising a plurality of stops positioned near the needle end of the sheath on the inner sheath wall to retain the needle transport assembly in a second position between the stops and the ampule when the needle is in use.

3. The assembly of claim 2, further comprising a pair of opposed locking cusps, each of said locking cusps arising from the sheath inner wall and projecting toward the sheath body end, the cusps adapted to lock the needle and needle assembly firmly in the third, locked and spent position following use of the needle.

4. A hypodermic needle assembly for a sharp, tubular needle which, in a sterile condition, is designed to penetrate the skin, the assembly comprising:

a syringe assembly comprising a cylindrical ampule having a chamber, a longitudinal axis, and an open end for receiving a plunger, the plunger adapted for sliding longitudinal movement within the chamber from the open end toward a converse end of the ampule having a small orifice for fluid communication with the tubular needle for entry and exit of fluids pulled into or forced from the ampule by movement of the plunger;

a one-piece safety sheath comprising a cylindrical tube with a longitudinal axis and an inner sheath wall, the sheath having an open needle end and an open sheath body end; the ampule and said sheath each having a diameter, and the diameter of the sheath slightly greater than diameter of the ampule, whereby the sheath is adapted to fit over and slide upon the syringe body;

a needle transport assembly comprising a luer having a front portion with an elongate channel to receive and fix the needle therein; and a back portion of the luer having a means for removably connecting the needle transport assembly to the syringe; a peripheral edge of transport assembly engaging the sheath inner wall; and, the needle and needle transport assembly adapted for movement within the sheath to a stop position, and the transport assembly having three temporarily fixed stop positions, a first, sterilized needle position; a second, needle in-use position; and a third, locked and spent needle position;

a means for anchoring the needle and needle transport assembly in a stop position, said means associated with the sheath and with the needle transport assembly;

wherein the safety sheath further comprises a needle end cap and a sheath body end cap, each of the caps adapted to alternately fit on and close an open end of the sheath to maintain the sterile condition of the needle within the sheath prior to use; for removal of the caps for opening the needle end of the sheath and sheath body end of the sheath at the time for use of the needle; and, for reclosing the sheath body for needle storage within the sheath following use;

further comprising a means for maintaining the needle and needle transport coaxial with the longitudinal axis of the sheath during in the course of the needle transport assembly movement;

wherein the means for maintaining comprises a pair of opposed elongated guide slots grooved on said inner wall of the sheath body and a pair of oppositely disposed guides, each guide projecting radially from on the transport assembly peripheral edge, and each of the slots adapted to receive a guide;

wherein the guide slots are grooved as longitudinal rectangularly shaped slots;

wherein the guides have a rectangular shape complimentary to shape of the slots; and, wherein the means for anchoring the needle and needle transport assembly in said first, sterilized needle position, said second, needle in-use position, and in said third, locked and spent needle position within the sheath comprises a pair of oppositely disposed cusps associated with the peripheral edge of said needle transport assembly, each cusp biased outward from the edge and adapted to interfit with a corresponding stop tab formed along the sheath inner wall for anchoring the needle transport assembly in the first, second position, and for locking the needle transport assembly in the third position.

5. The assembly of claim 4, wherein the syringe assembly further comprises a protruding column which surrounds the orifice and provides a nozzle for the ampule for fluid communication with back of the luer.

6. The assembly of claim 5, wherein the means for removably connecting of the luer comprises a cylindrical projection, which arises from the ampule and surrounds the column to form a needle transport receptacle; the receptacle having an inner wall with helical female fastener threads cut on said inner wall.

7. The assembly of claim 6, wherein the receptacle comprises a female double threaded bushing with a thread cut commencing on either side of the receptacle to maintain the needle in alignment coaxial with the longitudinal axis of the ampule.

8. The assembly of claim 7, wherein the back luer portion further comprises a cylindrical end with a head portion distal from the luer, the head having a pair of struts, each strut positioned on an opposite side of the head and projecting radially outward from the end portion, the struts adapted for insertion in the female fastener threads of the ampule and by rotating the sheath, for axial movement of the lure against the ampule.

9. The assembly of claim 7, wherein the cylindrical end of the luer has an outer wall with helical fastener threads cut on said outer wall.

10. The assembly of claim 8, wherein the sheath is constructed of a translucent material.

11. The assembly of claim 10, wherein the sheath is constructed of a transparent material.

12. The assembly of claim 11, wherein the luer is constructed of nylon.

* * * * *